US009926523B2

(12) United States Patent
Burns et al.

(10) Patent No.: US 9,926,523 B2
(45) Date of Patent: *Mar. 27, 2018

(54) CELL CARRIERS AND METHODS FOR CULTURING CELLS

(71) Applicant: General Electric Company, Schenectady, NY (US)

(72) Inventors: Andrew Arthur Paul Burns, Niskayuna, NY (US); David Gilles Gascoyne, Niskayuna, NY (US); Scott Michael Miller, Clifton Park, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 145 days.

This patent is subject to a terminal disclaimer.

(21) Appl. No.: 13/839,409

(22) Filed: Mar. 15, 2013

(65) Prior Publication Data

US 2013/0210140 A1 Aug. 15, 2013

Related U.S. Application Data

(63) Continuation-in-part of application No. 12/970,735, filed on Dec. 16, 2010, now abandoned.

(51) Int. Cl.
*C12M 1/32* (2006.01)
*C12N 5/00* (2006.01)

(52) U.S. Cl.
CPC ........... *C12M 23/12* (2013.01); *C12N 5/0068* (2013.01); *C12N 2533/30* (2013.01); *C12N 2535/10* (2013.01)

(58) Field of Classification Search
CPC ... C12N 5/0068; C12N 5/0606; C12N 5/0607
USPC .................................................... 435/305.1
See application file for complete search history.

(56) References Cited

U.S. PATENT DOCUMENTS

| | | | |
|---|---|---|---|
| 4,801,475 A | 1/1989 | Halpern et al. | |
| 4,906,237 A | 3/1990 | Johansson et al. | |
| 5,284,766 A | 2/1994 | Okano et al. | |
| 5,449,620 A | 9/1995 | Khillan | |
| 5,707,859 A | 1/1998 | Miller et al. | |
| 5,763,548 A | 6/1998 | Matyjaszewski et al. | |
| 5,800,412 A | 9/1998 | Zhang et al. | |
| 6,121,371 A | 9/2000 | Matyjaszewski et al. | |
| 6,190,913 B1 * | 2/2001 | Singh | 435/394 |
| 6,627,314 B2 | 9/2003 | Matyjaszewski et al. | |
| 6,720,469 B1 | 4/2004 | Curtis et al. | |
| 6,777,227 B2 | 8/2004 | Ricci et al. | |
| 6,790,919 B2 | 9/2004 | Matyjaszewski et al. | |
| 6,861,103 B2 | 3/2005 | Chang et al. | |
| 7,052,776 B2 | 5/2006 | Fanta et al. | |
| 7,354,704 B2 | 4/2008 | Malin et al. | |
| 8,148,111 B2 | 4/2012 | Kurokawa et al. | |
| 8,241,907 B2 | 8/2012 | Shogbon et al. | |
| 2002/0028493 A1 | 3/2002 | de Bruijn et al. | |
| 2002/0081726 A1 | 6/2002 | Russell et al. | |
| 2003/0003554 A1 | 1/2003 | Miller et al. | |
| 2003/0036196 A1 | 2/2003 | Okano et al. | |
| 2003/0162287 A1 | 8/2003 | Yamamoto et al. | |
| 2003/0219824 A1 | 11/2003 | Malin et al. | |
| 2004/0214326 A1 | 10/2004 | Cousins et al. | |
| 2005/0054101 A1 | 3/2005 | Felder et al. | |
| 2006/0165625 A1 | 7/2006 | Verrall et al. | |
| 2006/0205071 A1 | 9/2006 | Hasson et al. | |
| 2008/0009064 A1 | 1/2008 | Ronfard et al. | |
| 2008/0026464 A1 | 1/2008 | Borenstein et al. | |
| 2008/0187995 A1 | 8/2008 | Murphy et al. | |
| 2008/0199959 A1 | 8/2008 | Algotsson et al. | |
| 2008/0208351 A1 | 8/2008 | Besenbacher et al. | |
| 2009/0047260 A1 | 2/2009 | Van Dyke | |
| 2009/0069904 A1 | 3/2009 | Picha | |
| 2009/0098183 A1 | 4/2009 | Detamore et al. | |
| 2009/0228027 A1 | 9/2009 | Yamanaka et al. | |
| 2009/0248145 A1 * | 10/2009 | Chan et al. | 623/1.41 |
| 2009/0248157 A1 | 10/2009 | Dalby et al. | |
| 2009/0311735 A1 | 12/2009 | Crook et al. | |

(Continued)

FOREIGN PATENT DOCUMENTS

DE 102006012960 A1 9/2007
EP 0382214 B1 5/1995
(Continued)

OTHER PUBLICATIONS

Ewald et al.; Salt impregnation of implant materials; Oral Surg Oral Med Oral Pathol Oral Radiol Endod;107; pp. 790-795; Jun. 2009.*
Thormann et al., "Interactions between a Polystyrene Particle and Hydrophilic and Hydrophobic Surfaces in Aqueous Solutions", Langmuir, vol. 24, No. 14, 2008, pp. 7278-7284.
Manbachi et al. "Microcirculation within Grooved substrates regulates Cell positioning and Cell Docking inside Microfluidic Channels", Lab Chip, pp. 747-754, May 2008.
Melinex 454, XP-002672166, Downloaded from the Internet:<http://www.fly-supply.com/Melinex-Films/Melinex-454/Det> on Mar. 22, 2012, 1 Pages.
(Continued)

*Primary Examiner* — Antonio Galisteo Gonzalez
(74) *Attorney, Agent, or Firm* — Pabitra K. Chakrabarti

(57) ABSTRACT

A carrier for growing stem cells is provided, the carrier comprises a substrate comprising one or more outer surfaces; and a hydrophilic, water soluble coating material disposed and dried on one or more of the outer surfaces. The carrier comprises one or more structured indentations on one or more of the outer surfaces, wherein the carrier has a length at least about 0.2 mm, a width at least about 0.2 mm, and a height in a range from about 0.05 mm to 1.2 mm and each of the structured indentations has a major axis in a range from about 0.1 mm to 0.5 mm, a minor axis in a range from about 0.1 mm to 0.5 mm and a depth in a range from about 0.025 mm to about 0.5 mm. A method of culturing stem cells and stromal cells using the same carrier are also provided.

18 Claims, 4 Drawing Sheets

(56) References Cited

U.S. PATENT DOCUMENTS

Figure 1A:
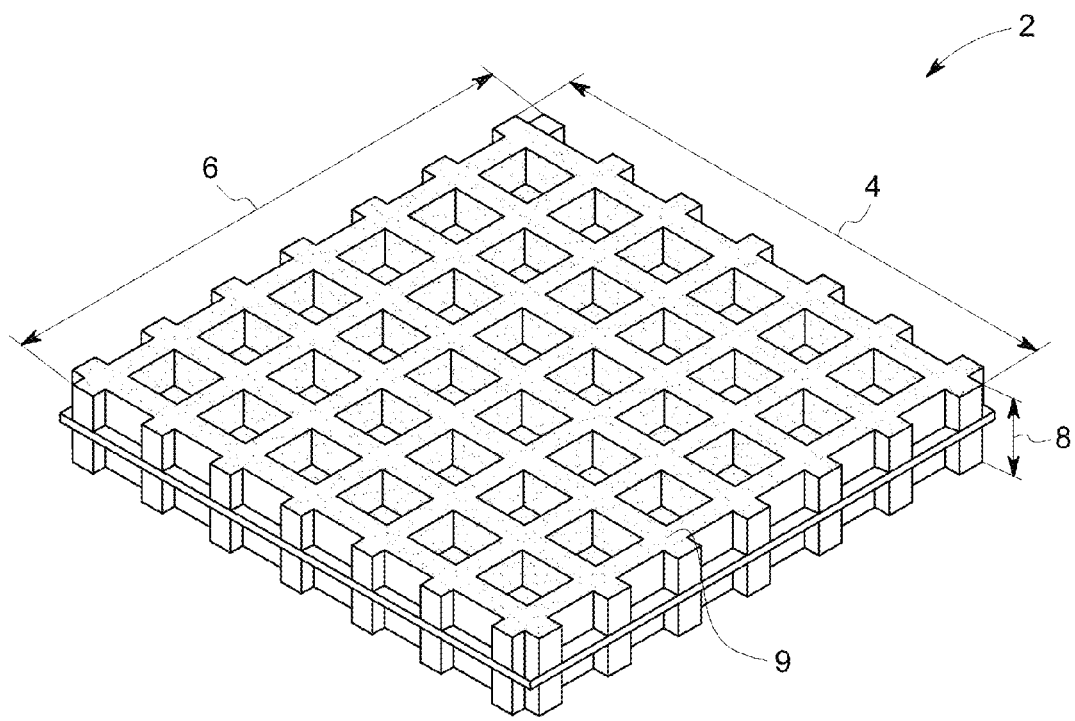

| | | |
|---|---|---|
| 2010/0093053 A1 | 4/2010 | Oh et al. |
| 2010/0124781 A1 | 5/2010 | Nelson |
| 2010/0136647 A1 | 6/2010 | Algotsson et al. |
| 2010/0197013 A1 | 8/2010 | Kamp et al. |
| 2010/0291674 A1 | 11/2010 | Beese et al. |
| 2010/0304482 A1 | 12/2010 | Deshayes et al. |
| 2010/0330674 A1 | 12/2010 | Rubinsztajn et al. |
| 2011/0027889 A1 | 2/2011 | McCarthy et al. |
| 2011/0076764 A1 | 3/2011 | Rubinsztain et al. |
| 2011/0104732 A1 | 5/2011 | Lucic et al. |
| 2011/0129919 A1 | 6/2011 | Oh et al. |
| 2011/0160869 A1 | 6/2011 | Duch et al. |
| 2011/0207209 A1 | 8/2011 | Hammons et al. |
| 2011/0207216 A1 | 8/2011 | Martin et al. |
| 2011/0275154 A1 | 11/2011 | Martin et al. |
| 2012/0045830 A1 | 2/2012 | Green et al. |
| 2012/0052579 A1 | 3/2012 | Shannon et al. |
| 2012/0058554 A1 | 3/2012 | Deshayes et al. |
| 2012/0058556 A1 | 3/2012 | Fabian et al. |
| 2012/0058561 A1 | 3/2012 | Sato |
| 2012/0156773 A1 | 6/2012 | Smith et al. |
| 2012/0156777 A1 | 6/2012 | Rangarajan et al. |
| 2012/0219531 A1 | 8/2012 | Oh et al. |
| 2014/0051163 A1 | 2/2014 | Healy et al. |

FOREIGN PATENT DOCUMENTS

| | | | |
|---|---|---|---|
| GB | 1079391 A | | 8/1967 |
| JP | 2004018556 A | | 1/2004 |
| JP | 2010057485 A | | 3/2010 |
| JP | 2010136706 A | | 6/2010 |
| WO | 99032595 A1 | | 7/1999 |
| WO | 2000070406 A1 | | 11/2000 |
| WO | 0162803 A2 | | 8/2001 |
| WO | 0192359 A1 | | 12/2001 |
| WO | 03055967 A1 | | 7/2003 |
| WO | 2004090506 A | | 6/2005 |
| WO | 2006033935 A2 | | 3/2006 |
| WO | WO 2007125288 A1 | * | 11/2007 |
| WO | 2008106771 A1 | | 9/2008 |
| WO | 2008140295 A1 | | 11/2008 |
| WO | 2009034186 A2 | | 3/2009 |
| WO | WO 2009105570 A2 | * | 8/2009 |
| WO | 2010094944 A1 | | 8/2010 |
| WO | 2011106032 A1 | | 9/2011 |
| WO | 2011147930 A1 | | 12/2011 |
| WO | 2012069841 A1 | | 5/2012 |

OTHER PUBLICATIONS

BD Biosciences, BD Biocoat—Dish 35MM PLL 5PAC 20CAS, 2010, Downloaded from the Internet<http://www.bdbiosciences.com/ptProduct.jsp?prodId=36494> on Mar. 16, 2012, 1 Page.

Collignon et al., "Integrity™ Xpansion™ Multiplate Bioreactor: The Scalable Solution for Adherent Stem Cell Expansion", ATMI LifeSciences, 2010, 1 page.

Fujita et al., "Time-lapse observation of cell alignment on nanogrooved patterns", Journal of Royal Society Interface, vol. No. 6, pp. 5269-5277; Feb. 25, 2009.

Funakoshi General Catalog 2005-2006 devices edition, pp. viii-ix, Dec. 22, 2005, 8 Pages.

Moeller et al., "A microwell Array system for stem cell culture", pp. 752-763, Nov. 14, 2007.

Cha et al., "Construction of Functional Soft Tissues From Premodulated Smooth Muscle Cells Using a Bioreactor System", Artificial Organs, vol. No. 30, Issue No. 9, pp. 704-707, Sep. 2006.

Cha et al., "Time-dependent Modulation of Alignment and Differentiation of Smooth Muscle Cells Seeded on a Porous Substrate Undergoing Cyclic Mechanical Strain", Artificial Organs, vol. No. 30, Issue No. 4, pp. 250-258, Apr. 2006.

Khorasani et al., "Plasma Surface Modification of Poly (I-Lactic acid) and Poly (lactic-co-glycolic acid) Films for Improvement of Nerve Cells Adhesion", Radiation Physics and Chemistry, pp. 280-287, vol. No. 77, Issue No. 3, Mar. 2008.

Kohen et al., "Characterization of Matrigel interfaces during Defined Human Embriyonic Stem Cell Culture", Biointerphases, pp. 69-79, vol. No. 4, Issue No. 4, Dec. 2009.

Korin et al., "Design of Well and Groove Microchannel Bioreactors for Cell Culture", Biotechnology and Bioengineering, vol. No. 102, Issue No. 4, pp. 1222-1230, May 1, 2009.

Lee et al., "Response of human chondrocytes on polymer surfaces with different micropore sizes for tissue-engineered cartilage", J Appl Polym Sci., vol. No. 92, pp. 2784-2790, 2004.

Jiang et al., "Fabrication of plastic microlens arrays using hybrid extrusion rolling embossing with a metallic cylinder mold fabricated using dry film resist", Optics Express, vol. No. 15, Issue No. 19, pp. 12088, Jan. 1, 2007.

Lindstrom et al., "High-Density Microwell Chip for Culture and Analysis of Stem Cells", PLoS One, vol. No. 4, Issue No. 9, pp. 1-9, Sep. 30, 2009.

Khabiry et al.; "Cell Docking in Double Grooves in a Microfluidic channel", 9 Pages, 2009.

Focke et al. "Lab-on-a-Foil: microfluidics on thin and flexible films", Lab on a Chip, vol. No. 10, pp. 1365-1386; Mar. 19, 2010.

McMurray et al., "Nanoscale surfaces for the long-term maintenance of mesenchymal stem cell phenotype and multipotency", Nature Materials, vol. No. 10, 8 Pages, Aug. 2011.

Satoh et al., "Cultivation of Human Induced Pluripotent Stem Cells with Controlled Aggregate Size and Geometrical Arrangement by Inverting Microwell Array Chip", 17th International Conference on Miniaturized Systems for Chemistry and Life Sciences, pp. 1701-1703, Issue No. 27-31, Oct. 2013.

Kessel et al., "Thermoresponsive PEG-based polymer Layers: Surface characterization with AFM force measurements", Langxmuir, vol. No. 26, Issue No. 5, pp. 3462-3467, 2010.

Huang et al., "Fast fabrication of integrated surface-relief and particle-diffusing plastic diffuser by use of a hybrid extrusion roller embossing process", Optics Express, vol. No. 16, Issue No. 1, pp. 440, Jan. 2008.

Ueda et al., "Substrates for Human Pluripotent Stem Cell Cultures in Conditioned Medium of Mesenchymal Stem Cells", Journal of Biomaterials Science, Polymer Edition, pp. 153-165, vol. No. 23, Issue No. 1-4, Apr. 13, 2012.

Kooten et al., "Plasma-treated polystyrene surface: model surfaces for studying cell-biomaterial interactions", Biomaterials; vol. No. 25, pp. 1735-1747, 2004.

Velten et al., "Investigations on reel-to-reel hot embossing", The international journal of advanced manufacturing technology, springer, berlin, DE, vol. No. 1-4, 24, pp. 73-80, Feb. 2009.

Velten et al., "Roll-to-Roll Hot Embossing of Microstructures", Design Test Integration and Packaging of MEMS/MOEMS (DTI P), pp. 326-331, 2010.

Wave Bioreactor Catalog2006, Wave Europe, pp. 1-13, 2006.

Yeo et al., "Micro-fabrication of polymeric devices using hot roller embossing"; Microelectronic Engineering, vol. No. 86, pp. 933-936, Dec. 2008.

International Search Report and Written Opinion issued in connection with related PCT Application No. PCT/EP2011/073065 dated Apr. 23, 2012.

International Search Report and Written Opinion issued in connection with related PCT Application No. PCT/EP2011/073061 dated May 2, 2012.

International Search Report and Written Opinion issued in connection with related PCT Application No. PCT/EP2011/073066 dated May 7, 2012.

International Search Report and Written Opinion issued in connection with related PCT Application No. PCT/EP2011/073064 dated May 9, 2012.

Unofficial English translation of Office Action and Search Report issued in connection with related CN Application No. 201180060701.9 dated May 6, 2014.

Unofficial English translation of Office Action issued in connection with related CN Application No. 2011800607019 dated Jul. 6, 2015.

(56) References Cited

OTHER PUBLICATIONS

Unofficial English translation of Office Action issued in connection with related JP Application No. 2013543815 dated Dec. 15, 2015.

* cited by examiner

CELL CARRIERS AND METHODS FOR CULTURING CELLS

CROSS REFERENCE TO RELATED APPLICATIONS

This application is a continuation-in-part of U.S. patent application Ser. No. 12/970,735, entitled "Cell carrier, associated methods for making cell carrier and culturing cells using the same", filed Dec. 16, 2010; which is herein incorporated by reference.

FIELD

The invention relates to cell carriers for culturing adherent cells, and associated methods for making and using the cell carriers. More particularly, the invention relates to polymer-based cell carriers with surface modifications to expand undifferentiated pluripotent or multipotent stem cells.

BACKGROUND

Pluripotent and multipotent stem cells have the potential to revolutionize various therapeutic applications, especially in the fields of regenerative medicine and pharmaceutical development. One of the obstacles for stem cell-based therapy is the requirement of large numbers of cells, which can be met by expanding stem cells without differentiation, culturing in a large scale. A number of technical hurdles remain for expansion of such cells using the currently available substrates for cell-culture.

Bioreactors have long been practiced as the preferred scale-up method for cell culture. The use of microcarriers for culturing adherent cells is common in industrial bioprocessing. Typical bioreactor vessels employ some means of agitation, such as internal impellers, rocking or shaking mechanisms to suspend the cells and allow mass transfer of nutrients, oxygen and metabolic waste products. The agitation can subject cells to high degrees of flow-induced stress that can damage cells, especially sensitive ones such as stem cells. Carriers that can protect stem cells from agitation-induced damage and provide better stem cell recovery have recently been developed. In some cases, macrocarriers are used to facilitate easy separation of the carriers from the cells during passaging, and preventing the formation of cell-carrier aggregates.

In a bioreactor, growing adherent cells on macrocarriers (mm-size) may be subject to an issue of carrier-floating in the medium. One reason that carriers can float in the medium may be due to entrapped air on the textured surface of the carriers. For example, the carriers with concave textured surface may entrap air and therefore are prone to carrier floating. The floating carriers have limited exposure to cells and culture media, which affects cell seeding and thereby cell culture and growth.

Therefore, the carriers or a method of making such carriers which has enhanced wettability without permanently altering the surface chemistry or changing the environment of cell growth is highly desirable. The development of cell carriers that increase wettability to facilitate adherent cell attachment, proliferation and release, maintaining the quality and desired characterization of the cells under reduced shear forces is a long felt need.

BRIEF DESCRIPTION

One embodiment of a carrier for growing stem cells comprises a substrate comprising one or more outer surfaces; and a hydrophilic, water soluble coating material disposed and dried on one or more of the outer surfaces.

An embodiment of a carrier for growing cells, comprises a substrate comprising one or more outer surfaces; wherein one or more structured indentations on one or more of the outer surfaces, and the carrier has a length at least about 0.2 mm, a width at least about 0.2 mm, and a height in a range from about 0.05 mm to 1.2 mm and each of the structured indentations has a major axis in a range from about 0.1 mm to 0.5 mm, a minor axis in a range from about 0.1 mm to 0.5 mm and a depth in a range from about 0.025 mm to about 0.5 mm, and a hydrophilic, water soluble coating material disposed and dried on one or more of the outer surfaces.

An example of a method for expanding stem cells, comprises providing a carrier for expansion of pluripotent stem cells, comprising: a substrate comprising one or more outer surfaces modified with a gas plasma treatment, corona discharge treatment, chemical functionalization, coating or combinations thereof; and a salt coating disposed on the one or more of the modified outer surfaces, wherein the carrier has a length at least about 0.2 mm, a width at least about 0.2 mm, and a height in a range from about 0.05 mm to 1.2 mm and each of the structured indentations has a major axis in a range from about 0.1 mm to 0.5 mm, minor axis in a range from about 0.1 mm to 0.5 mm and depth in a range from about 0.025 mm to about 0.5 mm; and seeding and expanding the stem cells.

DRAWINGS

Figure 1B:
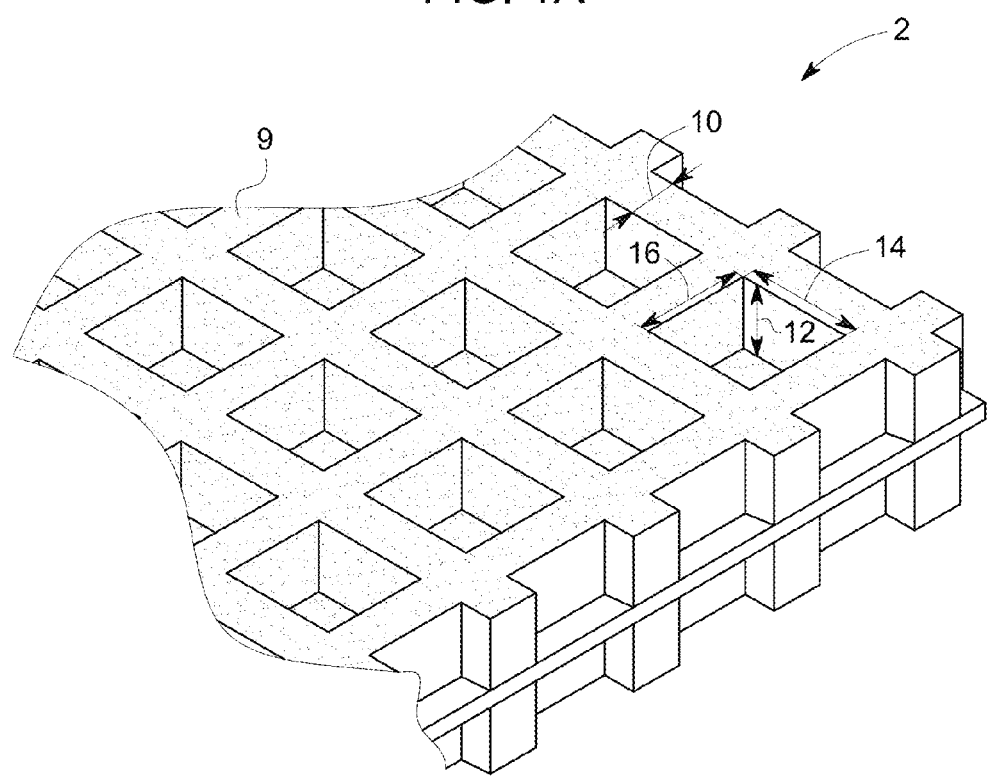

These and other features, aspects, and advantages of the present invention will become better understood when the following detailed description is read with reference to the accompanying drawings in which like characters represent like parts throughout the drawings, wherein:

FIG. 1A is an image of a carrier of the invention comprising a plurality of indentations showing dimensions of the carrier. FIG. 1B is an image of the same carrier showing dimensions of each indentation.

Figure 2A:
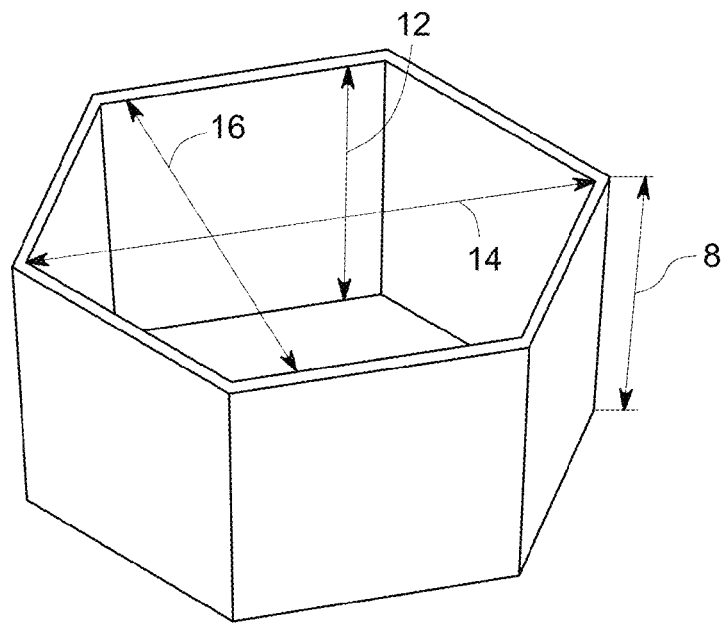
Figure 2B:
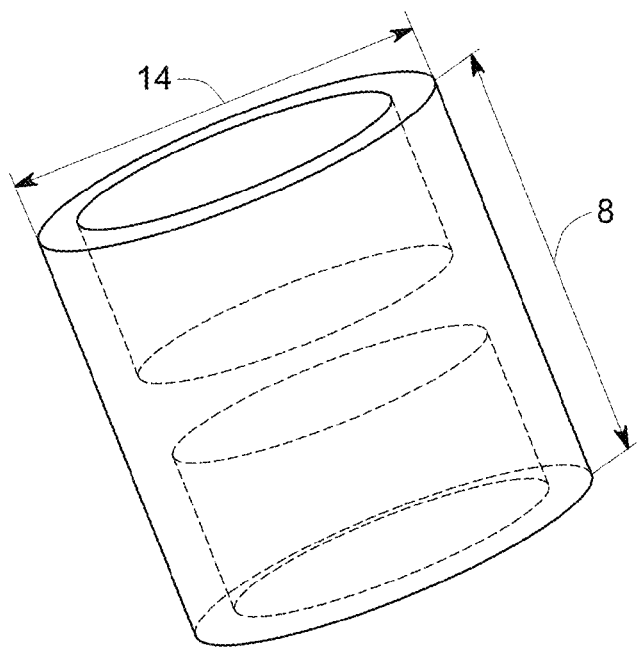
Figure 2C:
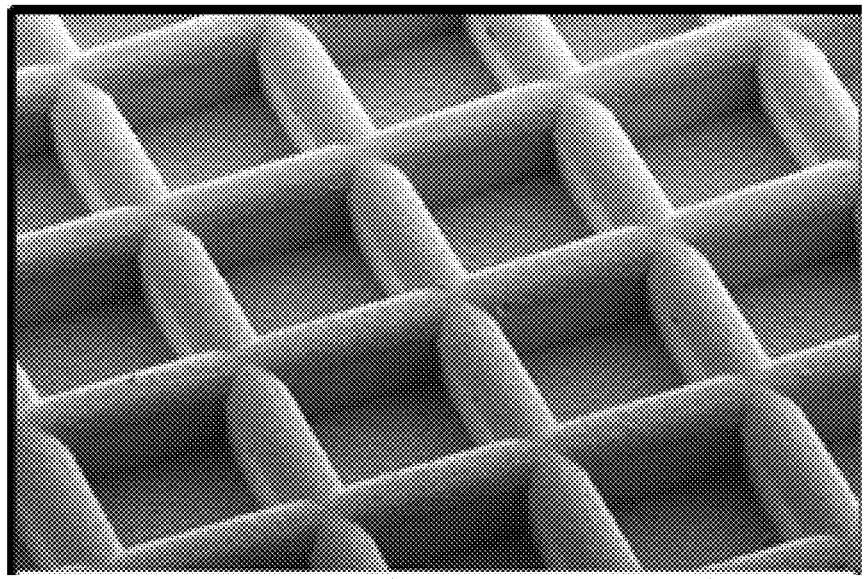
Figure 2D:
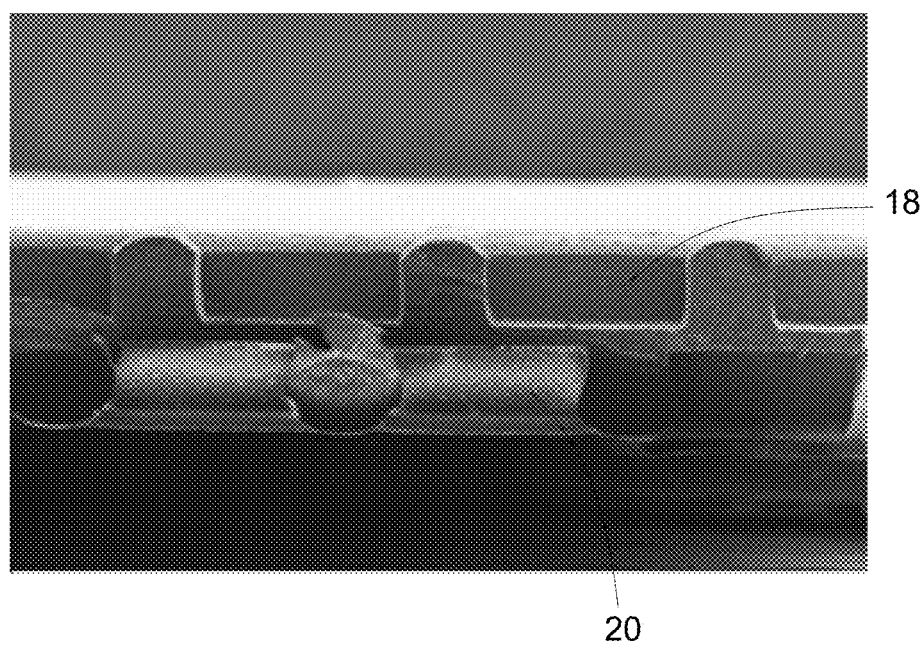

FIG. 2A is an image of a carrier of the invention comprising one indentation on one side of the base. FIG. 2B is an image of a carrier of the invention comprising one indentation each on two opposing sides of the base. FIG. 2C is a scanning electron microscope (SEM) image of a carrier of the invention comprising a plurality of indentations on one side of the base. FIG. 2D is an SEM image of a carrier of the invention comprising a plurality of indentations on both sides of the base.

Figure 3:
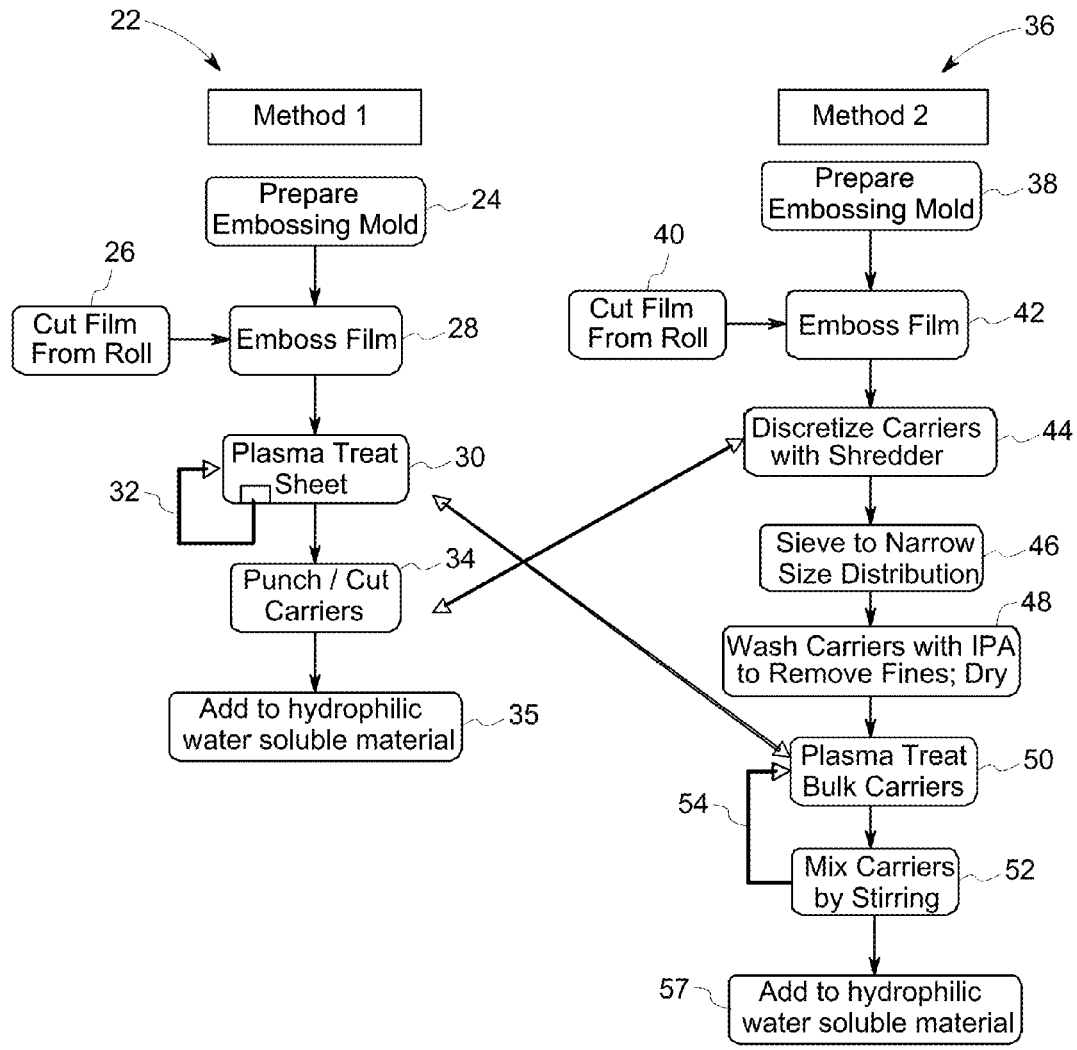

FIG. 3 is a process flow diagram of an example of methods of making carriers of the invention on a small scale in batch mode.

DETAILED DESCRIPTION

One or more of the embodiments of the invention relate to cell carriers for culturing pluripotent or multipotent stem cells, wherein the carriers are suspended in a bioreactor. The carrier may be modified by a surface treatment for better cell attachment, controlled growth and easy release. The surface treatment may include applying a coating material, gas plasma treatment, corona discharge treatment or combinations thereof.

To more clearly and concisely describe the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

A "carrier" or "carrier for growing cells", as referred to herein, is a support for adhering and culturing cells. The carrier may have indentations on it. Suitable materials of the carrier may include, but are not limited to, polymers, copolymers or blends of polymers. The carrier may further be coated with a suitable coating material for effective cell adherence and proliferation. The carrier may have one or more surface treatments, such as gas plasma treatment.

A "major axis", as referred to herein, is the longest dimension of each indentation present on the carrier surface. For example, for a rectangular indentation, length of the indentation is referred as the 'major axis'. A "minor axis", as referred to herein, refers to a dimension other than the longest dimension, of each indentation present on the carrier surface. For example, for a rectangular indentation, width of the indentation is referred as the 'minor axis'. For example, the major axis and minor axis are same for a square indentation as the length and width are same, as shown in FIGS. 1B, 14 and 16 respectively, the major axis of a circular indentation is a diameter as shown in FIGS. 2B, 14, the major axis is the length for a rectangular indentation, and the major axis is the major axis of an elliptical indentation.

An "aspect ratio", as referred to herein, is a ratio of depth to major axis of each structured indentation. For example, an aspect ratio for a circular indentation is a ratio of depth to diameter.

The carriers with textured surface, such as, indentations or pockets are prone to bubble entrapment when disposed in a liquid culture medium and thereby have a tendency to float in the medium. The carrier of the present invention comprises a coating, which increases the wettability of the carriers in a bioreactor to preclude bubble entrapment. The coating may comprise a hydrophilic, water soluble material, disposed and dried on the carrier surface. The enhanced wettability increases the accessibility of the carriers to the cells, which ensures cell seeding followed by efficient cell attachment and growth. Moreover, the coating dissolves during wetting and the underlying surface chemistry which interfaces with cells remains unchanged.

In one embodiment, a carrier for growing stem cells comprises a substrate comprising one or more outer surfaces and a hydrophilic, water soluble coating material disposed and dried on one or more of the outer surfaces. The carriers of the present embodiment comprise one or more outer surfaces and the surfaces are coated with hydrophilic, water soluble material that enhances wettability of the carriers.

One or more embodiments of a carrier for expansion of stem cells comprise a substrate comprising one or more outer surfaces. In some embodiments, the substrate may comprise a flat surface. In some other embodiments, the substrate comprises one or more structured indentations on one or more of the outer surfaces. In these embodiments, the carrier has a length of at least about 0.2 mm, a width of at least about 0.2 mm, and a height in a range from about 0.05 mm to 1.2 mm and each of the structured indentations has a major axis in a range from about 0.1 mm to 0.5 mm, a minor axis in a range from about 0.1 mm to 0.5 mm and a depth in a range from about 0.025 mm to about 0.5 mm. In some embodiments, the carriers with structured indentations and coated with hydrophilic, water soluble coating are suitable for growing embryonic stem cells (ESCs), adult stem cells (e.g mesenchymal stem cells), induced pluripotent stem cells, transdifferentiated cells or any adherent cells. As noted, the carriers of the present invention are coated with a hydrophilic, water soluble material, wherein the material is disposed on the carrier surface and dried before use.

As noted, the carrier for growing adherent cells, comprises one or more outer surfaces; and one or more structured indentations in one or more of the outer surfaces, wherein the carrier 2, as shown in FIG. 1A, has a length 4 of at least about 0.2 mm, a width 6 of at least about 0.2 mm, and a height 8 in a range from about 0.05 mm to 1.2 mm. In some embodiments, the carrier has a length 4 in a range from about 0.2 mm to 6.5 mm, a width 6 in a range from about 0.2 mm to 6.5 mm, and a height 8 in a range from about 0.05 mm to 1.2 mm. In some embodiments, the carrier has a width and length from about 0.2 to 25 mm. In some embodiments, the wall-thickness 10 of the carrier is in a range from about 0.05 mm to 2 mm. In some embodiments, the carrier comprises a surface 9, wherein the surface is treated with a hydrophilic, water soluble material to form a coating that increases wettability of the carriers.

Embodiments of the structured indentations, as shown in FIG. 1B, comprise a depth 12, a major axis 14, and a minor axis 16, wherein the major axis 14 of an indentation is in a range from about 0.1 mm to 0.5 mm, the minor axis 16 is in a range from about 0.1 mm to 0.5 mm, and the depth 12 is in a range from about 0.025 mm to about 0.5 mm. The wall-thickness 10 is in a range from about 0.05 mm to 2 mm. As used herein the term, 'depth' of an indentation refers to the depth of the inner wall of each indentation. As used herein, the term 'wall-thickness' refers to a thickness of a single wall for a carrier with single indentation, or thickness of each of the multiple walls for the carrier with a plurality of the structured indentations as shown in FIG. 1B. Each of the structured indentation has an aspect ratio in a range from about 0.1 to about 1.5. In some embodiments, the carrier comprises a surface 9, wherein the surface is treated with a hydrophilic, water soluble material to form a coating that increases wettability of the carriers.

In one embodiment, the carrier may comprise one indentation on at least one surface of the carrier as shown in FIG. 2A. In this embodiment, the carrier is a 'cup' like structure on one outer surface of the base with a continuous wall surrounding the base of the carrier. In an alternate embodiment, the carrier may comprise one indentation on each of the surfaces of the carrier as shown in FIG. 2B. In this embodiment, the carrier has two 'cup' like structures on opposing outer surfaces of the base with a continuous wall surrounding the cups. This carrier may be useful for specific cell culture conditions or for specific cell-types. The single carrier (FIGS. 2A and 2B) has a length in a range from about 0.1 mm to 6.5 mm, a width in a range from about 0.1 to 6.5 mm, and a height 8 in a range from about 1 mm to 10 mm, and a wall-thickness 10 of the carrier in a range from about 0.05 mm to 2 mm. In case of a single 'cup' (FIG. 2A) or two 'cups' on opposing sides of the base (FIG. 2B), has a length that is same as the major axis 14 as shown in FIGS. 2A and 2B, a width that is same as the minor axis 16, and the cup has a depth 12, as shown in FIG. 2A.

In some embodiments, the carrier comprises at least one surface for growing adherent cells, wherein more than one structured indentation is present on the surface, for example, the carrier has a plurality of structured indentations on an outer surface of the base, as shown an SEM image in FIG. 2C. The carrier, in one embodiment, comprises at least two outer surfaces. In this embodiment, more than one structured indentation is formed on each of the outer surfaces, such as 18 and 20 are the structured indentations on the upper and lower surface respectively, as shown in FIG. 2D. In this embodiment, the carrier has a plurality of indentations on opposing outer surfaces of the base (FIG. 2D).

In some embodiments, the carrier has a substantially planar disc-like structure. As used herein, 'substantially planar disc', refers to a disc, which provides a planar surface area for growing cells. The shape of the carrier may be polygonal. In one or more embodiments, the shape of the carrier may vary, for example, the carrier may have an overall perimeter that is circular, elliptical, triangular, rectangular, square, pentagonal, or hexagonal in shape.

The disc like-structure of the carrier may provide higher surface area per unit volume for culturing cells, relative to, e.g. spherical structures. The carrier size (both length and width of 0.2 to 6.5 mm) may allow about 4-100× fold of hMSC expansion per passage. The shape and size of the carrier may also allow about 2 to 50-fold of hESC expansion per passage. Efficient separation of released (e.g. enzymatic release using trypsin or accutase, etc) cells from the carriers is facilitated by significant size difference between the cells (~15 microns) and the carriers (larger than 0.2 mm). Released cells may be separated from the carriers via simple filtration, or separation of the supernatant after allowing the carriers to settle.

Each structured indentation has a wall that protrudes normal to the outer surface of the carrier, as shown in FIGS. 1A, 1B, 2A, and 2B. The wall height is chosen to balance the various requirements of the carrier, for example, a lower wall (i.e., shallow indentation) allows higher packing density of carriers per unit volume, and therefore can provide higher cell yield per unit volume of reactor. Moreover, transport of oxygen, nutrients and metabolic waste to/from the cells is facilitated at lower wall heights (i.e., shallower indentations). However, a higher wall (i.e., deeper indentation) can offer higher degrees of protection from hydrodynamic forces arising due to agitation inside the bioreactor. Further, a higher wall or deeper indentation can provide a microenvironment that prevents dilution of any cell-secreted molecules. This may be advantageous if cell-cell signaling or autocrine factors are a desired part of the cell culture or processing operations. The desired range of the height of the wall projected above the plane of the carrier is therefore optimized with these factors in mind, in a range from 0.05 mm to 1.2 mm; in some embodiments from about 0.05 mm to about 0.5 mm, or in some embodiments, from about 0.08 mm to about 0.2 mm.

The carrier of the present invention comprises a hydrophilic, water soluble coating that increases the wettability without permanently altering the surface chemistry of the carrier or changing the environment for cell culture. As noted, the coating is made of hydrophilic, water soluble material to enhance the carrier wettability. The water influx into the pockets of the carriers removes the trapped air from the pockets. The coating material may be biocompatible and unlikely to affect the growth conditions of the cells. In one or more embodiments, the coating comprises salts, saccharides, amphiphiles, hydrophilic polymers, cell culture media constituents or combinations thereof.

In one embodiment, the salt coating comprises sodium chloride. In some embodiments, the carriers are immersed in a sodium chloride solution and dried before use. The coating of sodium chloride increases the wettability of the carrier as the coating is hydrophilic in nature. The salt is added during the final washing step in carrier production as either an aqueous or aqueous alcohol solution, which is decanted prior to thorough drying in a vacuum oven. A thin, crystalline layer of salt left on the carrier surface may enhance wettability by creating a driving force for the dissolution of salt which draws water across the surface, and into the pockets. The coating is water soluble, and therefore the salt coating dissolves in the culture media. In some embodiments, the coated surface may be used in conjunction with a medium which requires further salt. In this embodiment, as culture media requires a specific concentration of salt for cell growth, the coated surface has an amount of salt, which provides a required salt concentration to the culture medium after dissolution. In some embodiments, the coated surface has an amount of salt which does not deleteriously affect the osmolality (ionic strength) of the solution. In one embodiment, the sodium chloride may be present on the carrier surface in a concentration in a range from about 0.01% to 3% by a mass of sodium chloride with respect to a mass of the carrier. Determination of osmolality of a biological media on addition of salt-coated carriers via vapor pressure osmometry indicates that there is no substantial change in osmolality of the media within the aforementioned range.

An alternative embodiment of the coating material includes amphiphilic molecules such as non-ionic or polymeric surfactants. The carriers may be disposed in a solution of amphiphilic molecules followed by drying, which may provide a coating of amphiphiles on the surface. The amphiphilic molecules may enhance the wettability of the carriers by decreasing the surface energy of the polymer surface. In one or more embodiments, the amphiphiles comprise polymers, surfactants, lipids, fatty acids or combinations thereof. In some embodiments, the amphiphile-coated carriers are washed before cell-seeding. In some embodiments, the amphiphiles are soluble in water, and may dissolve in the culture media without affecting cell growth. In some embodiments, the polymers or surfactants present on the coated surface may dissolve in culture media and become part of the media constituents.

In some embodiments, the coating comprises a saccharide. The saccharide may be monosaccharide, disaccharide or polysaccharide. The polysaccharide may comprise glucose, fructose, maltose, dextrose or combinations thereof. The saccharide coating also provides a hydrophilic surface of the carrier, which helps in wetting the carriers in the liquid medium. Though the saccharide is water soluble, it may not appreciably change the concentration of nutrient constituents, pH or salt concentration of the culture media during cell culture. Moreover, saccharides are generally biocompatible materials which do not have any detrimental effects on the cells.

As noted, in one embodiment, the coating comprises cell culture media constituents. A further embodiment of the coating comprises use of non-biologic media constituents. The media constituents form a hydrophilic, water soluble coating that increases the wettability of the carrier without changing the environment for cell culture. In one embodiment, the media constituents are added as a coating material in a concentrated form. This would enable an end user to mix the dried carriers with water to reconstitute the media along with the carriers. In this embodiment, the biological components, such as serum, proteins, vitamins, nutrients, minerals or salts, may be added to prepare the desired culture media. In one or more embodiments, the culture media constituents are non-protein materials. For example, the culture media constituents may comprise inorganic salts (e.g., NaCl, $CaCl_2$, $Fe(NO_3)_3$, KCl, $Mg(SO_4)$, $NaH_2PO_4$), amino acids, vitamins, pH indicators (phenol red), sodium pyruvate, or a glucose source. Incorporating a full or partial dry media mix may enable workflow simplification and standardization of the procedure by incorporating the media into the reactor which reconstitutes on mixing with water, which may require agitation and a high salt concentration, both of which may be beneficial to carrier wetting.

The present embodiments of the coated carriers prevent carrier flotation without changing the carrier surface chemistry, which may significantly affect cell seeding and/or growth. The manufacturing process for carriers may include several wash steps. A final wash step may be added or a final wash step may be substituted, wherein the carriers are washed with one of the desired coating solutions, such as a salt solution. The wash step with a coating solution prior to vacuum drying has a minimal impact on the manufacturability of the carriers. Further, the coating solution is generally decanted/aspirated off prior to the final drying. The removal of excess coating solution may allow for control of the actual molar amount of salt added to the carriers, which may be minimal. In some embodiments, the carrier surface is dried incubating at room temperature for longer duration, such as two to three weeks, without heating.

In some embodiments, aqueous solutions of salt, surfactant, polymer or other coating materials may be used. In some other alternate embodiments, an alcohol is added to the solution, which may be beneficial at least in three ways. First, the addition of alcohol lowers the surface tension of the liquid, which facilitates complete wetting of the carrier in the solution and results in uniform deposition of the coating material over the surface of the carrier. Second, the addition of a large volume fraction (>50%) of alcohol (ethanol, 2-propanol, methanol, etc.) to the solution prevents growth of the microorganisms which may contaminate the cell carriers or may leave endotoxin on the carrier surface. Third, the incorporation of an alcohol, such as, methanol, ethanol, 2-propanol, decreases the time required for drying the carriers prior to use or packaging because of the higher vapor pressure of alcohol compared to water.

Following dissolution and/or desorption of the hydrophilic coating material, the carriers are generally in suspension inside a bioreactor, comprising a fluid having a convective motion that generates sufficient transport of nutrients and oxygen to cells to enable growth. The cells adhere to the surface of the structured indentations having a flat or curved wall of sufficient height such that the effect of fluid-induced hydrodynamic stress on the cells is minimized. The carrier comprises an optimum depth of indentations, balancing the needs of the adherent cells providing access to nutrients and metabolites, while protecting the cells from exposure to hydrodynamic shear generated by fluid motion.

Unlike other adherent cells, the pluripotent stem cells, such as hESCs may adhere poorly to a polymeric surface due to cell phenotype or culture conditions. The surface treatment may improve the cell attachment, growth and controlled differentiation. The surface treatment may include plasma treatment, coating, surface functionalization or combinations thereof. The plasma treated surface may result in faster and more robust cell attachment on cell carrier and results in higher cell yields than an untreated surface.

In some embodiments, one or more surfaces of the carriers are modified with plasma treatment. As noted, the hydrophilic, water soluble coating material may be disposed on the plasma treated carrier surface. In some embodiments, the hydrophilic water soluble coating is disposed on non-plasma treated surface. One or more other coating materials may be disposed on the hydrophilic water soluble coating, which may further be plasma treated. In some embodiments, the polymer-based carrier surfaces are modified with functional groups or coatings to enable better cell attachment and growth. The plasma treatment may be broadly categorized into at least two types: one is an atmospheric plasma treatment in which an electrical energy source is combined with atmospheric gases to create reactive plasma. Another treatment comprises vacuum plasma treatment wherein a DC electrical energy source or an AC (e.g, radio frequency) energy source is used in combination with a vacuum chamber and containing pressurized gases including oxygen, nitrogen, argon, nitrous oxide, carbon dioxide, carbon monoxide, ammonia or combinations thereof to create a reactive plasma. In some embodiments, a surface treatment is imparted to the embossed polymer film comprising one or more of corona discharge treatment, gas plasma treatment, chemical functionalization, coating or combinations thereof.

In one or more embodiments, the surface modification may be achieved via plasma treatment. The plasma treatment on each of the surfaces may modify the surface property of the carriers, e.g. hydrophobicity, hydrophilicity or wettability. Wettability may be quantified by contact angle measurements. The increased hydrophilicity of plasma treated carriers is known to improve cell attachment and growth compared to growth on untreated polymer surfaces. In some embodiments, the plasma treatment may comprise gas plasma treatment. The gas plasma treatment may impart surface chemistry through the introduction of oxygen, nitrogen, carbon dioxide, nitrous oxide, ammonia or combinations thereof. In some embodiments, the flat polystyrene films are plasma treated with two pure gases such as oxygen and ammonia, either sequentially, or as a gas mixture of oxygen and ammonia. The plasma treatment typically increases the oxygen content of the surface, introducing hydrophilic ketone, carboxylate and hydroxide moieties on the surface. The modified surface chemistry may help in adsorption of extracellular matrix proteins (ECM) such as fibronectin, fibrinogen, vitronectin, laminin, etc., which enhances cell attachment and cell proliferation on the treated surface.

One index of hydrophobicity or hydrophilicity is the contact angle of a water droplet on the surface. Contact angle can be measured by techniques well-known in the art. For example, a measurement of the water contact angle formed on a plasma treated flat polystyrene film is proportional to the degree of hydrophilicity imparted by the plasma treatment. In one or more embodiments, the water contact angle for the plasma treated carrier surface may be in a range from about 10° to about 90°. In some embodiments, the water contact angle for the plasma treated carrier surface is from 30° to 70°. The water contact angle increases over time after plasma treatment due to surface chemistry reorganization to an equilibrium state. The plasma treatment further provides a surface chemistry with long-term stability.

In some embodiments, the plasma treatment may be carried out in a plasma reactor. The plasma reactor may be a vacuum vessel with a gas at low pressure, typically 10 to 1000 mTorr. When a high frequency electric field is generated in the reactor, plasma is formed containing reactive species like ions, free radicals and vacuum-UV photons. These species may react with the polymer surface and may cause chemical modifications accompanying with corresponding changes in various properties, which depend on the nature of the gas and the plasma parameters. Gases such as oxygen, ammonia and argon are typically used for modification of the polymer surfaces. In some embodiments, carbon dioxide, nitrous oxide, ammonia or nitrogen is used for plasma treatment. In one embodiment, the polymer surface is modified by oxygen-plasma treatment to increase the cytophilicity of the surface. The surface functionality may also be altered via wet chemical methods such as oxidation treatments using perchloric acid or permanganate or partial hydrolysis using strong acids or bases.

In addition to gas type, the plasma system has different factors, such as process settings that can be varied. In one or more embodiments, the factors include chamber pressure, device power (50-2000 W), excitation frequency, duration, gas flow rate and plasma mode. The chamber pressure, device power, excitation frequency, duration and gas flow rate are continuous factors, which are maintained during the whole procedure. The plasma mode in some systems may be set to either reactive ion etch (RIE) or plasma etch (PE) mode, with the reactive ion etch mode as one of the desired modes in these embodiments.

In some embodiments, the surfaces are treated with corona discharge to modify one or more surface properties of the carriers. The hydrophilic water soluble material, such as salt, saccharides, amphiphiles or combinations thereof, may be deposited and dried on the corona treated surface to increase the wettability of the carriers. In corona discharge treatment, a current develops from an electrode with a high potential in a neutral gas, such as air. Ionization of the gas generates a layer of plasma around the electrode. The ions generated eventually pass the charge to nearby areas of lower potential, or recombine to form neutral gas molecules. Surfaces of organic films such as polystyrene, polyesters and others may be oxidized when exposed for a short time to the reactive air plasma generated by corona discharge. Corona discharge treatment can increase the oxygen content on the polymer surface and improve the film wettability by water.

The hydrophilic water soluble material, such as salt, saccharides, amphiphiles or combinations thereof, may be deposited and dried on the carriers, which further comprises a biomolecular coating. The biomolecular coating may specifically facilitate the adhesion and growth of stem cells. The embodiments of the carriers may comprise a coating that provides a xeno-free alternative to feeder cell layers. The present embodiments of the carriers provide feeder-free, and in some embodiments chemically defined coatings, which are useful for culturing cells that may safely be used for therapeutic applications.

A variety of biomolecules may be used to modify the carrier surfaces to enhance cell attachment. In some embodiments, the hydrophilic water soluble material coated carriers are further coated with biomolecules, such as macromolecules. In these embodiments, the macromolecular coating is disposed on the hydrophilic water soluble material coated surface to further increase cytophilicity. In some embodiments, the macromolecular or peptide coating is disposed on the plasma treated surface, which is further treated with hydrophilic water soluble material. In some other embodiments, the non-plasma treated carriers are coated with biomolecules, such as proteins or peptides. In these embodiments, the protein or peptide coating is directly disposed on the carrier surface. The biomolecule coated carriers may further comprise a coating of hydrophilic water soluble material.

One or more embodiments of the carrier comprise a macromolecular coating comprising biologically derived proteins or peptides, or synthetic macromolecules. In one embodiment, the macromolecular coating comprises extracellular matrix (ECM) proteins, proteoglycans, factors derived from a mouse sarcoma cell line or combinations thereof. In some embodiments, the biologically derived proteins may include various structural proteins such as collagen, laminin, entactin, vitronectin or fibronectin. In some embodiments, the coating comprises biomimetic or synthetic macromolecules, such as recombinant proteins. The recombinant proteins may include laminin 511 or laminin 521. In one embodiment, the surfaces are modified with recombinant fibronectin to enhance surface cytophilicity for better attachment of the cells. In some embodiments, cells are attached to extracellular matrix (ECM) through integrin, which is cell adhesion receptor that supports cell proliferation and differentiation. Integrin can bind to ECM proteins, such as collagen, fibronectin, vitronectin, laminin and N-linked glycoproteins.

The coating may further comprise natural polypeptides or synthetic polypeptides. In one or more embodiments, the coating further comprises growth factors that promote differentiation or proliferation of pluripotent or multipotent cell types. The coated surfaces support adhesion and expansion of stem cells in their undifferentiated state or directed differentiation into specialized cell types. One or more embodiments of the coating may comprise growth factors such as bFGF, TGF [3], Human Insulin, Human Holo-Transferrin, Human Serum Albumin, Glutathione or combinations thereof. In some embodiments, the synthetic peptide comprises the RGD sequence. Several of the ECM proteins include RGD peptide sequences and the cells can be attached through RGD binding via integrin to enable undifferentiated proliferation of hESCs in serum-free media.

The hydrophilic water soluble material treated carriers may be compatible with coatings used for hESC, such as, Matrigel™ or Synthemax® II. In one embodiment, the coating comprises Matrigel™, which is used as an attachment substrate for culturing embryonic stem cells. In this embodiment, the Matrigel™ coated carrier is further coated with hydrophilic water soluble material, such as a salt. In the absence of feeder cells, the embryonic stem cells are grown using Matrigel™ which comprises extracellular matrix components derived from the extracellular matrix material of a mouse sarcoma cell line (Engelbreth-Holm-Swarm). The Matrigel™ is heterogeneous in composition, containing different structural proteins including laminin, entactin and collagen with adhesive peptide sequences. Matrigel™ contains numerous other proteins in different amounts and its exact composition may vary. In examples, the coating material for culturing hESC may include Laminin521 or Synthemax® II. The coated carriers are compatible with gamma sterilization. The Laminin521 or Synthemax® II coated carriers may further comprise a coating of salt, which may increase the wettability of the carriers.

In some embodiments, the polymer coated carrier is further coated with hydrophilic water soluble material, such as salt. The carrier surface may be modified, for example, to enhance cell release as well as cell attachment. The coating may be made, for example, of a thermoresponsive polymer, pH responsive polymer, or combination thereof. Thermoresponsive polymers may include, but are not limited to, poly (N-isopropylacrylamide) (PNIPAM), poly(di(ethyleneglycol)methylether methacrylate) (PDEGMA). pH responsive polymers may include, but are not limited to, copolymers of acrylic acid, dimethylaminoethylacrylate, and hydroxyethylacrylate. The coating may comprise one or more layers. In some embodiments, where the coating comprises multiple layers, the layers may be homogeneous or heterogeneous. For one example, one layer may be made of thermoresponsive polymer, and another layer may be made of pH responsive polymer. Thermoresponsive or pH responsive polymer coatings on the surface can facilitate easy release of cultured cells from the carrier surface.

The structured indentations may also form relief features on the carrier surface. The relief features may be present on one or more surfaces of the carriers, which prevent the carriers from sticking to each other. Carrier sticking or clumping has been seen to be an issue with certain types of flat or smooth carriers during low shear mixing. The relief features on the carrier also serve to prevent the carriers from sticking to the inner walls of the reactor or culture vessel, which facilitates cleaning the reactors/culture vessels between batches of cell culture.

A cross sectional profile of each indentation may have, as non-limiting examples, a polygonal, a circular, or an elliptical shape. Each of the polygonal indentations may have, as non-limiting examples, a triangular, rectangular, square, pentagonal or hexagonal shape. The dimension of the major axis and minor axis of the indentations may be the same or different.

The carrier may be made of glass, polymer, ceramic, metal or a combination thereof. In one embodiment, the carrier is made of a polymer or a copolymer or a blend of polymers. The polymers may comprise, but are not limited to synthetic and natural polymers such as, polyester including polyethylene terephthalate (PET), polystyrene, polycarbonate, polyamide, polyurethane, olefin polymer, dextran, silicone, or polyacrylate, polymethacrylate or copolymer or blend of polymers thereof. In one specific embodiment, the carrier is made of polystyrene.

The polymer may be transparent, which allows cell observation under an optical microscope. In certain embodiments, the carrier has a substantially planar disc shape, which facilitates cell visualization by preventing lensing effects. Refraction of light can be a hindrance to visualization of cells on spherical carriers of certain refractive index. Cell visualization is useful, for example, for culturing and monitoring cells during stem cell expansion. In some embodiments, the polymer and surface treatment is substantially free of components of animal origin. This is especially beneficial in therapeutic applications, e.g., in the production of cells for cellular therapies. The polymer may be rigid at room temperature or cell culture temperature, non-porous and may have non-swelling properties in water, PBS or growth medium. The rigid, non-swelling, non-porous properties of the polymer can facilitate cell release, for example, when using standard enzymatic release protocols.

An example of a method of making a carrier for growing cells comprises providing a plurality of flat films and laminating the flat films to form a solid support. The solid support is subjected, to a method such as embossing, casting thermoforming, or injection molding to form structured indentations. In some embodiments, the solid support is embossed to form an embossed solid support, and the embossed solid support is cut into a plurality of portions or pieces to form a plurality of carriers. The plurality of embossed carriers is further treated with plasma to form plasma treated embossed carriers. In some other embodiments, the solid support is embossed to form structured indentations and make an embossed solid support, which is further treated with a plasma to form a plasma treated embossed solid support, followed by cutting or dicing the plasma treated embossed solid support to a plurality of portions or pieces to form a plurality of carriers. In one example, the embossing of the solid support is performed using a mold.

In one example, a process for making a carrier for growing cells is generally illustrated in FIG. 3. The process comprises two alternate methods, method (1) and method (2). The method (1) 22 comprises the steps of preparing an embossing mold 24, and cutting a film from a roll 26, followed by embossing the film 28. The embossed film is then treated with plasma 30 to form plasma treated embossed solid support. In some embodiments, the embossed film is optionally plasma treated on the other side of the film for better uniformity of treatment 32. The plasma treated embossed film is then diced or otherwise discretized into a plurality of carriers 34. The plurality of carriers are further added to a solution of hydrophilic water soluble material 35, to form a coating on the carrier surface.

The method (2) also may comprise a method 36 comprising the steps of preparing embossed mold 38, and cutting a film from a roll 40, followed by embossing the film 42. In some embodiments, the embossed film is obtained from a source and then the film is processed to cut the films into small pieces. The embossed film is cut or diced or otherwise discretized to generate embossed pieces 44, which can then be sieved to a narrow size distribution 46. In some embodiments, the carriers are then washed with a wash fluid such as water or a mixture of water and alcohol to remove fine particles, followed by drying 48. The carriers are then subjected to a plasma treatment 50 in bulk accompanied by mixing to ensure uniformity of surface treatment 52 to form plasma treated embossed carriers. The plasma treated carriers are then washed with a wash fluid such as water or a mixture of water and alcohol to remove fine particles. The plurality of carriers, after washing, further subjected to coating by adding to a solution of hydrophilic water soluble material 57 followed by drying, which forms a coating on the carrier surface. The methods (1) and (2) (as described above 22 and 36) can be modified to produce carriers on large scale using roll-to-roll operations for some or all of the steps of manufacturing. For example, the embossing or structure generation step can be scaled-up into a roll-to-roll operation, and the plasma treatment operation can be done in bulk in drum-style treaters, and the discretization can be done via roll-to-roll or sheet-fed cutting operations.

Another example of a method for making the carriers comprises initially providing two flat polymer films. The method further comprises forming one or more structured indentations on the two flat polymer films individually on at least one surface of each of the two films, such as by embossing to make two embossed polymer films (embossed on one side each), and laminating the two embossed polymer films together, back to back, to form a composite laminated embossed polymer film, so that the outwardly facing surfaces comprise one or more of the structured indentations. The laminated embossed polymer film may then be diced to form a plurality of untreated carriers. The untreated carriers are then treated with a plasma treatment to form a plurality of plasma treated carriers. To create structured indentations, the flat polymer films may be alternatively be subjected to casting thermoforming, or injection molding, or a bulk polymer may be made into a solution and cast on a mold to form a film with the structured indentations. In another embodiment, a method comprises initially providing two polymer films with embossed structure on one side (surface) of the film. These two films are provided, laminating the two embossed polymer films together, back to back, to form a composite laminated embossed polymer film, so that the outwardly facing surfaces comprise one or more of the structured indentations.

The structured indentations may be formed in the carrier by one or more of the following methods. In one example, a textured roll is used to make the structured indentations on a heated polymer film in a roll-to-roll process. In another example, a flat mold is prepared by cutting or machining the negative of the desired indentations into a metal block. The metal block then may be used as-is or replicated first as a positive and then as a negative, using, for example, a polymer casting process. The negative mold can then be used in a batch-stamping or hot embossing process to emboss the pattern into a polymer film. In another example, a mold thus formed can be used in a solvent-casting process to make the polymer film with the structured indentations. A polymer solution can be coated on to the mold or textured roll, and dried and/or cured. The dried/cured film then peeled off to yield a film with the desired structured indentations. Alternate methods such as thermoforming or injection molding may also be used.

The embossed carriers may be washed with one of the desired hydrophilic water soluble coating solution, such as a salt solution. The coating solution is generally decanted or aspirated off prior to using the drying means. The carriers are dried by vacuum drying. The removal of excess coating solution may control the actual molar concentration of salt, and retains the concentration as required for the culture medium.

A cell culture system of the invention uses one or more of the carriers for growing cells. In one embodiment, the cell culture system is a bioreactor, more specifically, an agitated bioreactor. As mentioned herein, a bioreactor may refer to any device or system that supports cell growth. In one aspect, a bioreactor may refer to a device or a system for growing cells or tissues in the context of cell culture or tissue engineering. The bioreactor may employ agitation, generated by an internal impeller or paddle, or via externally rocking, rolling or shaking the culture vessel, or via bellows-induced motion of fluid. The bioreactor may, for example, be a reactor with rocking or rolling motion, such as Wave Bioreactor™, a stirred tank bioreactor, a fluidized bed bioreactor, fixed bed bioreactor, a roller bottle or airlift bioreactor.

The Wave Bioreactor™ comprises a rocking platform supporting a vessel containing a culture fluid, wherein the culture fluid comprises cells in a culture media. The rocking motion of the platform induces mixing and mass transport in the culture fluid. A stirred tank bioreactor generally comprises an impeller system and optionally a sparging system to mix and aerate the culture. An airlift reactor relies on rising gas bubbles to mix and aerate the culture medium. Hydrodynamic factors such as mass transfer, mixing efficiency, and shear stress experienced by cells can be different in the different types of bioreactors. In addition, the cell growth rate and quality of cells may be influenced by operational differences between reactor types.

In another embodiment, the bioreactor may be a stirred tank bioreactor which, under operational condition, comprises a vessel containing the cell growth medium, cells, and carriers. The carriers are agitated through the use of a mechanically or magnetically actuated paddle, screw, impeller or other rotational device (or devices) for mixing the contents of the reactor. Specifically, it is beneficial to ensure that the impeller is raised to a sufficient height above the bottom of the reactor that it does not directly impinge on the bed of carriers. The arrangement of impellers which are raised to a sufficient height above the bottom of the reactor provides two benefits, first, it prevents cells on the carriers from interacting directly with the impeller and generating high local shear and second, it prevents the carriers from becoming bound between the impeller and the vessel walls which may cause high local shear, carrier breakage and hinder proper mixing of the media. Finally, as opposed to traditional bioreactor growth, where shear is not as great of an issue, intermittent, low rate stirring is beneficial in these embodiments as it limits the total amount of potential shear stress on the cells.

The Corning disposable spinner flask is a stirred tank reactor that consists of a 125 mL or 500 mL reservoir, an impeller (paddle) and integrated magnet. The unit comes presterilized, eliminating the need for time-consuming assembly or cleaning and reassembly. The paddle size and height is optimized for different vessel size or volume. The spinner flasks sit on a magnetic induction stirrer that controls the stir rate and provides smooth and even rotation of the impeller. Thus, the hydrodynamic factors including fluidization of the carriers and shear stress can be controlled.

An example of a method of culturing adherent cells comprises providing one or more carriers for growing cells in a bioreactor, adding culture medium, adding an inoculum of cells to the carriers, allowing attachment of cells to the carriers, suspending the carriers in the medium continuously or intermittently, and allowing the cells to grow on the carriers. Cells may be grown in a culture flask or plate prior to addition to the carriers. Cells may also be grown on the carriers directly after extraction and isolation, for example, from blood, bone marrow or tissue section. In some other embodiments, the carriers may be introduced into a spinner flask, a stacked culture flask, a stirred tank reactor, a Wave Bioreactor™ or any other in-vitro cell culture system.

Cultured cells may be detached or released from the carriers by a variety of methods. The cells may be released, for example, by using a mechanical method, an enzyme, a thermoresponsive polymer, a pH responsive polymer or a combination thereof. The cell release by mechanical method includes cell scraping. The cells may also be released by treating with proteolytic enzymes, such as trypsin or accutase. One non-enzymatic method uses calcium chelators, such as EDTA. Other non-enzymatic methods include, but are not limited to, physical methods that use ultrasound, which generates bubbles that facilitate cell detachment. Cultured cells from carriers comprising thermoresponsive polymers, such as poly-N-isopropylacrylamide (PNIPAAm) may be released by cooling the carrier to a temperature below the lower critical solution temperature (LCST).

The carriers can be used in combination with a bioreactor or culture vessel, to provide or enhance surface area for the attachment and growth of anchorage-dependent cells. Some embodiments of the kit of the invention for culturing cells comprise a disposable housing or vessel pre-loaded with one or more carriers. In one embodiment, the carriers and the disposable housing or vessel may be provided separately. In one embodiment, the housing may be reusable. The housing may be, for example, a bag, a flask, a tank, a tube, a petridish or a bottle. The kit may further comprise culture media suitable for cell growth. The kit may comprise cells in a frozen condition and may further comprise a protocol for using the carriers.

The present embodiments provide culture and release of adult stem cells and pluripotent stem cells with high purity, high efficiency and high yield. The carriers used in these embodiments incorporate plasma treated textured surfaces that may protect adherent, shear-sensitive cells, such as human adult stem cells (e.g., mesenchymal stem cells, hMSC) and human pluripotent stem cells (hPSCs) which include human embryonic stem cells (hESC) or human induced pluripotent stem cells (hiPSC). In one or more embodiments, human pluripotent stem cells (e.g. embryonic stem cells) are seeded onto the polystyrene carriers, which protect the cells from fluid induced shear that may result in cell death and differentiation, specifically when the cells are cultured in a bioreactor. In the absence of shear forces, the hESCs may be able to grow and expand more readily while maintaining their stem cell phenotype. In one or more embodiments, the carriers are easily separable from the cultured hESCs. The density of the carriers may be slightly higher than the density of the growth medium.

The cell culture carrier of the present invention may greatly extend the proliferative capacity of different primary cells isolated from tissues and various stem cells from bone marrow, cord blood, adult blood, or adipose tissue. The expansion of such cells greatly facilitates various applications, such as, transplantation, tissue engineering, etc. using autologous or allogeneic cell sources. Sufficient expansion and recovery of adult stem cells may overcome the limitations of using adult stem cells for various applications. The sufficient recovery of adult stem cells can replace the embryonic stem cells which may address the ethical issues of using embryonic stem cells for various applications.

Example 1. Fabrication of Carrier for Growing Cells

Method of Making a Pattern Master—

A pattern-master was prepared by cutting grooves in a flat aluminum block using a dicing saw, which is outfitted with a resin-bonded diamond blade. A set of parallel grooves (the term being interchangeably used with 'indentations') was first cut in one direction, then a second set of parallel grooves was cut perpendicular to the first set of grooves. Finally, an effort was made to remove burrs that had formed in the first set of grooves during the cutting process. After the grooves were completed, the aluminum block was cleaned to remove any burrs on its surface. The pattern master determined the pattern geometry of the embossed carriers.

Formation of First Generation Mold from the Pattern Master—

A first-generation mold was then made from the pattern-master using a fluorosilicone rubber, FSL 7661 (purchased from Momentive Performance Materials, Waterford, N.Y.). To produce the first-generation mold, the two part fluorosilicone compound was mixed at a 1:1 ratio according to directions from the manufacturer, using a Hauschild Speed-Mixer. The pattern-master was placed in a hollowed-out Teflon block and uncured fluorosilicone was applied, in excess, on the surface of the pattern master. A chrome-plated steel plate was placed on top of the fluorosilicone, and the fluorosilicone was cured in a heated hydraulic press at 4000 lb force and 170° C. for 30 minutes. After cooling to room temperature, the cured fluorosilicone rubber-based first-generation mold was removed from the pattern-master and cured overnight at 200° C. in air.

Formation of Second Generation Mold from the Pattern Master—

Two second-generation molds were then prepared using a silicone rubber-molding compound, RTV 664 (purchased from Momentive Performance Materials, Waterford, N.Y.) from the first-generation mold as mentioned above. The silicone compound was mixed at a 10:1 ratio according to directions from the manufacturer, using a Hauschild Speed-Mixer. The first-generation mold was placed inside a steel frame with the patterned surface up and the silicone compound was dispensed, in excess, on the first-generation mold. A flat stainless steel plate was placed on top of the silicone and the silicone was cured in a heated hydraulic press at 1000 lb force and 120° C. for 30 minutes. After cooling to room temperature, the cured silicone rubber second-generation mold was removed from the fluorosilicone first-generation mold.

Method of Making Embossed Polystyrene Sheets—

Multiple sheets of biaxially oriented polystyrene film (Trycite 1003U, Dow Chemical Company) were placed in between two second-generation molds with patterns facing in. The number of sheets of film was chosen so that the volume of polystyrene was sufficient to fill the pattern in the second-generation molds and still leave a small amount of polystyrene separating the molds. The films were then embossed (28, FIG. 3) in a heated hydraulic press with 1000 lb force and a temperature cycle that ramped up to 150° C. for 5 minutes and then cooled to below 60° C. The embossing process fused the multiple sheets of film into a single monolithic structure that replicated the texture of the molds and pattern-master on both sides. The embossed polystyrene film was removed from the molds after cooling to room temperature.

Chemical Treatment of the Embossed Film Surface—

To make the embossed polystyrene film compatible with cell growth, the film was $O_2$ plasma treated (30, FIG. 3) using a Plasma Therm SLR vacuum plasma reactor as mentioned in FIG. 3. Plasma treatment was performed on each side of the embossed film for 1 minute at 100 mtorr pressure using 100 sccm (Standard Cubic Centimeters per Minute) $O_2$ flow and 100 W forward radio frequency (RF) power in reactive ion etching (RIE) mode.

Dicing of the Film to Generate Carrier—

Carriers for cell culture were prepared from the plasma-treated embossed sheets either by manually cutting the film into 5 mm×5 mm pieces or 2 mm×2 mm pieces, or by discretizing (44) and then sieving (46) to select a particular size range, or by punching circular discs of the desired size.

Variants of the Carrier Fabrication Process—

In some instances, a ceramic block was used in place of the aluminum block to make the pattern-master. A pattern-master was prepared by cutting grooves in a flat alumina block (99.6% alumina, fired, 20-25 μm polish from Acumet) using a dicing saw outfitted with a resin-bonded diamond blade. A set of parallel grooves was first cut in one direction, and then a second set of parallel grooves was cut perpendicular to the first set of grooves. The geometry of the pattern master determined the pattern geometry of the eventual embossed carriers. When the ceramic block was used, the first-generation mold was prepared slightly differently. Instead of the Teflon block, a steel frame was used to hold the ceramic pattern-master. The curing was performed at a higher temperature, 170° C. for 15 minutes and then 200° C. for 15 minutes. The rest of the procedure remained the same as described above.

In some examples, the fluorosilicone first-generation molds were replaced with RTV silicone first-generation molds. The procedure was modified as described below. A first-generation mold was then made from the pattern-master using a silicone rubber-molding compound, RTV 664 from Momentive Performance Materials. To produce the first-generation mold, the silicone compound was mixed at a 10:1 ratio according to directions from the manufacturer, using a Hauschild SpeedMixer. The pattern-master was placed in a hollowed-out Teflon block and uncured silicone compound was applied, in excess, across the surface of the pattern master. A chrome-plated steel plate was placed on top of the silicone, and the silicone was cured in a heated hydraulic press at 1000 lb force and 120° C. for 30 minutes. After cooling to room temperature, the cured silicone rubber first-generation mold was removed from the pattern-master. The first generation mold was coated with (tridecafluoro-1, 1,2,2-tetrahydrooctyl) trichlorosilane by vacuum deposition at 750 mtorr for 45 minutes prior to making any second-generation molds. Cell carriers of different designs were made using the above fabrication procedures. The embossed cell carriers of the invention may include carriers with alternate wall shape.

Alternatively, carrier fabrication was accomplished by extruding a film and embossing it in a roll-to-roll process. The produced film was patterned on both sides with 650 nm pitch waffle pattern (450 nm square well size with a depth of 200 nm) and cut into hexagonal pieces (0.25" edge-to-edge width). Carriers were plasma treated as a 1135 g batch in a commercial rotating drum plasma system with a central rod anode. The plasma was generated at 500 W with a 1000 sccm flow of $O_2$ for 18 minutes with a rotation rate of ~5 rpm. Carriers were stored at room temperature and ambient humidity for approximately one month before aliquots were prepared (5.85 g/batch) in polypropylene 50 mL centrifuge tubes (Corning).

Example 2 Aqueous NaCl Coating of Plasma Treated Polystyrene Carriers

Materials:

The materials used for the subsequent examples include centrifuge tubes, disposable spinner flasks and Synthemax® II substrates purchased from Corning® (MA, USA). Matrigel™ matrix was purchased from BD Biosciences. Laminin 521 was purchased from BioLamina (Stockholm, Sweden). Accutase™ was purchased from MP Biomedical (CA, USA) and Invitrogen™ (NY, USA); TrypLE was purchased from Invitrogen (NY, USA). mTeSR™-1 medium was purchased from STEMCELL™ Technology Inc. (Vancouver, BC, Canada). Y-27632 (ROCK Inhibitor) was purchased from Sigma Aldrich (St. Louis, Mo.) and Millipore®.

Cell Carriers—

The carriers used for the following examples had a length and width of 6.5 mm, and a height of about 0.5 mm. The carriers comprised a plurality of structured indentations on each of the two outer surfaces. Each of the structured indentations had a major axis and minor axis of 0.45 mm each and a depth of 0.2 mm.

Cells:

Human embryonic stem cells, such as CT-2 cell line was obtained from University of Connecticut, USA; CHB-10 cell line was obtained from George Daley, Children's Hospital Boston, USA; and the H1 and H7 cell lines were obtained from Geron Corporation. Human mesenchymal stem cells, catalog number PT-2501 were purchased from Lonza Poietics.

Carriers were roll-to roll embossed on both sides with 650 nm pitch waffle pattern (450 nm square well size with a depth of 200 μm) and cut into hexagonal pieces (0.25" edge-to-edge width). Carriers were plasma treated as a 1135 g batch in a commercial rotating drum plasma system with a central rod anode. The plasma was generated at 500 W with a 1000 sccm flow of $O_2$ for 18 minutes with a rotation rate of ~5 rpm. Carriers were stored at room temperature and ambient humidity for approximately one month before aliquots were prepared (1.17 g/batch) in polypropylene 50 mL centrifuge tubes (Corning).

A 110 mM solution of NaCl in $H_2O$ was prepared and diluted 1:10 and 1:100 with 18.2MΩ deionized water. Carriers were washed thrice with 25 mL isopropanol, thrice with 25 mL deionized water and twice with 25 mL 70% (v/v) ethanol in water. Finally, the carriers were suspended in 25 mL of the neat or diluted salt solution and after vigorous mixing for 30 seconds, the solution was poured off. The remaining solution (1.8-2.3 g liquid) was dried onto the carriers in a vacuum oven at ~5 Torr and a temperature of 40° C. for a minimum of 3.5 hrs (or until no further mass loss was apparent). After drying, the residual salt was between 0.01 and 1.0% of the mass of the carriers (0.012 mg-1.878 mg) and was dispersed over the carrier surface as thin crystals.

Carriers were resuspended in alpha-MEM medium with nucleosides and Glutamax along with 15% FBS (Gibco) at a ratio of 50 mL medium per 1.17 g aliquot of carriers by gently pouring the medium down the side of a 125 mL magnetically stirred bioreactor (Corning #3152) and the carriers were assessed immediately after medium addition, and then manually swirled until all carriers were sunk. The time to sink was monitored and compared to washed, unsalted carriers. The carriers washed in the highest concentration of salt (110 mM) sank rapidly, with approximately 90% of the carriers sinking during medium addition. The remainder sank with between 5 and 7 seconds of agitation. The carriers washed in 10-fold lower salt concentration (11 mM) exhibited a larger number of initial floating carriers, but all were sunk with between 4 and 6 seconds of agitation. The carriers washed in the lowest salt concentration (1.1 mM) exhibited about 25% floating carriers, and required between 11 and 14 seconds of agitation to get complete sinking.

For comparison, a washed and dried aliquot of carriers oxygen plasma treated four hours prior to testing (exhibiting a contact angle of ~5-10° exhibited rapid sinking with 4-5 seconds of agitation. An aliquot of carriers which was allowed to equilibrate for at least a month after plasma treatment exhibited ~25% floating carriers and required more than 20 seconds of vigorous agitation to fully submerge the remaining carriers.

To determine the concentration at which the addition of salt to the carrier surface could potentially affect cell growth, osmolality measurements were performed on a benchtop osmometer for each of the above samples. At 110 mM, the osmolality of the medium rose to 318±4 mmol/kg from the baseline medium value of 302±2.5 mmol/kg. Both of the lower concentrations exhibited no appreciable rise in osmolality (in the range 300±2.5 mmol/kg).

Example 3—Aqueous Ethanolic NaCl Coating of Plasma Treated Polystyrene Carriers and Subsequent Human Embryonic Stem Cell Growth Carriers were roll-to-roll embossed on both sides with 650 nm pitch waffle pattern (450 nm square well size with a depth of 200 μm) and cut into hexagonal pieces (0.25" edge-to-edge width). Carriers were plasma treated as a 1135 g batch in a commercial rotating drum plasma system with a central rod anode. The plasma was generated at 500 W with a 1000 sccm flow of $O_2$ for 18 minutes with a rotation rate of ~5 rpm. Carriers were stored at room temperature and ambient humidity for approximately one month before aliquots were prepared (1.17 g/batch) in polypropylene 50 mL centrifuge tubes (Corning).

A 110 mM solution of NaCl in $H_2O$ was prepared and diluted 1:5 with a 50/50 volumetric mixture of ethanol (200 proof non-denatured, Pharmco) and water. Carriers were washed thrice in 25 mL of isopropanol, thrice in 18.2MΩ deionized water and thrice in the prepared salt solution. As a control, an aliquot of carriers was prepared without a salt coating (final washes in 70% Ethanol/H2O). Both sets of carriers were decanted to remove the free liquid and the remaining solution was dried onto the carriers in a vacuum oven (5 Torr, 40° C.) for at least 3 hours. Aliquots were heat sealed in polyethylenepolyethylene (LDPE) bag and shipped out for gamma sterilization (25 kGy). After gamma sterilization, carriers were resuspended in phosphate buffered saline solution in a 125 mL bioreactor (Corning #3152) and coated with 7 mL of Matrigel (BD) diluted 1:20 in DMEM/F12 for 60 minutes with mixing every 20 minutes, followed by 0 or 1 washes with PBS.

Human embryonic stem cells (CT-2 cell line, University of Connecticut) were grown on a Matrigel™ (BD) coated 6-well tissue culture polystyrene plate for at least one passage prior to this experiment. Cells were washed once with phosphate buffered saline (PBS) and treated with Accutase™ (MP Biomedical) for three minutes at 37° C. Cells were centrifuged at 200 G for 5 minutes and resuspended in mTeSR-1 medium. Cells were counted on a NucleoCounter NC-100 (Chemometec, Denmark).

The cells were seeded onto the Matrigel™-coated carriers in the spinner flask at a concentration of $3 \times 10^6$ cells/100 $cm^2$ projected surface area (1.17 g aliquot) in 50 mL mTeSR-1 medium. The cells were stirred continuously for 15 minutes at 60 rpm to encourage seeding after which they were stirred on a 1 minute on, 45 minute off cycle at 40 rpm. Half of the media volume was removed on the second day after seeding, and the cells were harvested on the third day after seeding. For harvest, the media was removed, followed by a PBS wash, followed by the addition of 7 mL of Accutase™ which was gently stirred and returned to the incubator for six minutes. The suspended cells were removed and the carriers washed with PBS to remove the remaining cells. The cells were then centrifuged at 200 g for 5 minutes and resuspended in mTeSR-1 for counting via NucleoCounter NC-100. For the non-salt-coated carriers, $32 \times 10^6$ live cells were recovered, for a fold expansion of 10.9 with a viability of 94%. For the salted carriers, $29 \times 10^6$ cells were recovered, for a fold expansion of 9.8 with a viability of 92%. Based on the known variability of growth for these cells, these two values may be considered identical within error, showing that there are no deleterious effects on cell growth for salt-coated, gamma-treated carriers.

Example 4—Aqueous Ethanolic NaCl Coating of Plasma Treated Polystyrene Carriers and Subsequent Human Mesenchymal Stem Cell Growth Carriers were roll-to-roll embossed on both sides with 650 nm pitch waffle pattern (450 nm square well size with a depth of 200 μm) and cut into hexagonal pieces (0.25" edge-to-edge width). Carriers were plasma treated as a 1135 g batch in a commercial rotating drum plasma system with a central rod anode. The plasma was generated at 500 W with a 1000 sccm flow of O2 for 18 minutes with a rotation rate of ~5 rpm. Carriers were stored at room temperature and ambient humidity for approximately one month before aliquots were prepared (5.85 g/batch) in polypropylene 50 mL centrifuge tubes (Corning).

A 110 mM solution of NaCl in $H_2O$ was prepared and diluted 1:5 with a 50/50 volumetric mixture of ethanol (200 proof non-denatured, Pharmco) and water. Carriers were washed thrice in 25 mL of isopropanol, thrice in 18.2MΩ deionized water and thrice in the prepared salt solution. As a control, an aliquot of carriers was prepared without a salt coating (final washes in 70% Ethanol/$H_2O$). Both sets of carriers were decanted to remove the free liquid and the remaining solution was dried onto the carriers in a vacuum oven (5 Torr, 40° C.) for at least 3 hours. Aliquots were heat sealed in an LDPE bag and shipped out for gamma sterilization (25 kGy). After gamma sterilization, carriers were re-suspended in phosphate buffered saline solution and transferred to a 125 mL bioreactor (Corning #3152) with mesenchymal stem cell medium comprising alpha-MEM with Nucleosides and GlutaMax (Invitrogen) with 15% fetal bovine serum (FBS).

Human mesenchymal stem cells (Lonza Poietics—PT-2501) were grown on a polystyrene T-flask for at least one passage prior to this experiment in alpha-MEM medium supplemented with 10% MSC-qualified FBS (Invitrogen, 12763-025). Cells were washed once with phosphate buffered saline (PBS) and treated with Accutase™ (MP Biomedical) for five minutes at 37° C. Cells were centrifuged at 200 G for 5 minutes and re-suspended in mesenchymal stem cell medium. Cells were counted on a NucleoCounter NC-100 (Chemometec, Denmark).

The cells were seeded onto the carriers in the spinner flask at a concentration of 4000 cells/square cm projected surface area ($2 \times 10^6$ per 5.85 g of carriers) in 100 mL alpha-MEM medium supplemented with 15% MSC-qualified FBS. The cells were stirred on a 1 minute on, 45 minute off cycle at 45 rpm. The full medium volume was replaced on the fourth day after seeding, and the cells were harvested on the eighth day after seeding. For harvest, the media was removed, followed by a PBS wash, followed by the addition of 25 mL of Trypsin which was gently stirred and returned to the incubator for fifteen minutes. The suspended cells were removed and the carriers washed with PBS to remove the remaining cells. The cells were then centrifuged at 200 g for 5 minutes and re-suspended in mTeSR-1 for counting via NucleoCounter NC-100.

For the non-salt-coated carriers, $4.8 \times 10^6$ live cells were recovered, for a fold expansion of 2.4. For the salted carriers, $5.3 \times 10^6$ cells were recovered, for a fold expansion of 2.7. Based on the known variability of growth for these cells, these two values may be considered identical within error, showing that there are no deleterious effects on cell growth for salt-coated, gamma-treated carriers.

Example 5—Aqueous Coating of Plasma Treated Polystyrene Carriers with a Surfactant Carriers were roll-to-roll embossed on both sides with 650 nm pitch waffle pattern (450 nm square well size with a depth of 200 μm) and cut into hexagonal pieces (0.25" edge-to-edge width). Carriers were plasma treated as a 1135 g batch in a commercial rotating drum plasma system with a central rod anode. The plasma was generated at 500 W with a 1000 sccm flow of $O_2$ for 18 minutes with a rotation rate of ~5 rpm. Carriers were stored at room temperature and ambient humidity for approximately one month before aliquots were prepared (1.17 g/batch) in polypropylene 50 mL centrifuge tubes (Corning).

Pluronic F-68 (BASF) is a non-ionic surfactant comprised of a triblock copolymer of poly ethylene oxide/poly-2-propylene oxide/poly ethylene oxide with a total molecular weight of approximately 8500 g/mol. F-68 is commonly used in biology to reduce viscosity of high cell-content growth media. It is generally regarded as safe and is available in GMP grades. Thus, we considered it as a possible material for enhancing carrier wetting.

A 2% (mass/volume) solution of F-68 in $H_2O$ was prepared and diluted 1:10 and 1:100 with 18.2MΩ deionized water. Carriers were washed thrice with 25 mL isopropanol, thrice with 25 mL deionized water and twice with 25 mL 70% (v/v) ethanol in water. Finally, the carriers were suspended in 25 mL of the neat or diluted F-68 solution and after vigorous mixing for 30 seconds, the solution was poured off. The remaining solution (1.9-2.4 g liquid) was dried onto the carriers in a vacuum oven at ~5 Torr and a temperature of 40° C. for a minimum of 3.5 hrs (or until no further mass loss was apparent). After drying, the residual mass was between 0.005 and 0.40% of the mass of the carriers (0.4-32 μg).

Carriers were re-suspended in alpha-MEM medium with nucleosides and Glutamax along with 15% FBS (Gibco) at a ratio of 50 mL medium per 1.17 g aliquot of carriers by gently pouring the medium down the side of a 125 mL magnetically stirred bioreactor (Corning #3152) and the carriers were assessed immediately after medium addition, and then manually swirled until all carriers were sunk. The time to sink was monitored and compared to washed, unsalted carriers. The carriers washed in the highest concentration of F-68 (2% m/v) sank rapidly, with approximately 90% of the carriers sinking during medium addition. The remainder sank with between 8 and 10 seconds of agitation. The carriers washed in 10-fold lower F-68 concentration (0.2% m/v) exhibited similar performance, while the least coated carriers behaved similar to untreated, aged carriers described below.

For comparison, a washed and dried aliquot of carriers oxygen plasma treated four hours prior to testing (exhibiting a contact angle of ~5-10° exhibited rapid sinking with 4-5 seconds of agitation. An aliquot of carriers which was allowed to equilibrate for at least a month after plasma treatment exhibited ~25% floating carriers and required more than 20 seconds of vigorous agitation to fully submerge the remaining carriers.

To determine the concentration at which the addition of salt to the carrier surface could potentially affect cell growth, osmolality measurements were performed on a benchtop osmometer for each of the above samples. The baseline medium value of 302±2.5 mmol/kg was used as a benchmark. The osmolality of even the highest concentration F-68 material showed no appreciable change in osmolality (300±2 mmol/kg).

Example 6—Aqueous Coating of Medium Components on Plasma Treated Polystyrene Carriers Carriers are roll-to-roll embossed on both sides with 650 nm pitch waffle pattern (450 nm square well size with a depth of 200 μm) and cut into hexagonal pieces (0.25" edge-to-edge width). Carriers are plasma treated as a 1135 g batch in a commercial rotating drum plasma system with a central rod anode. The plasma is generated at 500 W with a 1000 sccm flow of $O_2$ for 18 minutes with a rotation rate of ~5 rpm. Carriers are stored at room temperature and ambient humidity for approximately one month before aliquots were prepared (1.17 g/batch) in polypropylene 50 mL centrifuge tubes (Corning).

The powdered mixtures are prepared, added to cell culture grade water to form a basic medium, and titrating with 1 (N) NaOH to achieve the desired pH. Such powdered media generally contain inorganic salts (e.g., NaCl, CaCl2, Fe(NO3)3, KCl, Mg(SO4), NaH2PO4), amino acids, vitamins, pH indicators (phenol red), sodium pyruvate, and a glucose source (glucose). These components are dissolved in water and dried along with the carriers, such that the carriers are coated in dried medium components and become re-suspended during rehydration of the medium.

A solution of medium constituents in $H_2O$ is prepared and diluted 1:10 and 1:100 with 18.2MΩ deionized water. Carriers are washed thrice with 25 mL isopropanol, thrice with 25 mL deionized water and twice with 25 mL 70% (v/v) ethanol in water. Finally, the carriers are suspended in 25 mL of the neat or diluted solution of medium and after vigorous mixing for 30 seconds, the solution is poured off. The remaining solution (1.8-2.3 g liquid) is dried onto the carriers in a vacuum oven at ~5 Torr and a temperature of 40° C. for a minimum of 3.5 hrs (or until no further mass loss is apparent). After drying, the residual medium constituent is dispersed over the carrier surface.

Example 7—Aqueous Coating of Saccharides Medium Components on Plasma Treated Polystyrene Carriers Carriers are embossed on both sides with 650 nm pitch waffle pattern (450 nm square well size with a depth of 200 μm) and cut into hexagonal pieces (0.25" edge-to-edge width). Carriers are plasma treated as a 1135 g batch in a custom-made rotating drum plasma system with a central rod anode. The plasma is generated at 500 W with a 1000 sccm flow of $O_2$ for 18 minutes with a rotation rate of ~5 rpm. Carriers are stored at room temperature and ambient humidity for approximately one month before aliquots were prepared (1.17 g/batch) in polypropylene 50 mL centrifuge tubes (Corning).

A solution of glucose in $H_2O$ is prepared and diluted 1:10 and 1:100 with 18.2MΩ deionized water. Carriers are washed thrice with 25 mL isopropanol, thrice with 25 mL deionized water and twice with 25 mL 70% (v/v) ethanol in water. Finally, the carriers are suspended in 25 mL of the neat or diluted solution of glucose and after vigorous mixing for 30 seconds, the solution is poured off. The remaining solution (1.8-2.3 g liquid) is dried onto the carriers in a vacuum oven at ~5 Torr and a temperature of 40° C. for a minimum of 3.5 hrs (or until no further mass loss is apparent). After drying, the residual medium constituent is dispersed over the carrier surface.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A carrier for growing stem cells, wherein the carrier is configured to be held in a suspended state in a solution in a bioreactor, and wherein the carrier is configured to protect the stem cells from exposure to hydrodynamic shear generated by a fluid motion in the bioreactor, comprising:

a substrate comprising two outer surfaces, wherein one or more structured indentations are present on the two outer surfaces of the substrate; and a hydrophilic, water soluble coating material disposed and dried on the two outer surfaces, wherein the carrier has a length from about 0.2 mm to about 25 mm, a width of from about 0.2 mm to about 25 mm, and a height in a range from about 0.5 mm to about 1.2 mm, and wherein each of the structured indentations has a major axis in a range from about 0.1 mm to about 0.5 mm, a minor axis in a range from about 0.1 mm to about 0.5 mm, a depth in a range from about 0.025 mm to about 0.5 mm, and an aspect ratio in a range from about 0.1 to about 1.5, and wherein the coating material comprises a sodium chloride, and the concentration of sodium chloride is in a range from about 0.01% to about 3% by mass with respect to a mass of the carrier.

2. The carrier of claim 1, wherein each of the structured indentations comprises a cross sectional profile of a polygonal shape, a circular shape, or an elliptical shape.

3. The carrier of claim 1, wherein the carrier is made of a glass, a polymer, a ceramic, a metal, or combinations thereof.

4. The carrier of claim 1, wherein the carrier is made of dextran, silicone, polyester, polycarbonate, polyamide, polyurethane, olefin polymer, or polyacrylate polymer.

5. The carrier of claim 1, wherein the carrier is made of polystyrene.

6. The carrier of claim 1, wherein the carrier comprises a perimeter that is triangular, rectangular, square, pentagonal, hexagonal, circular, or elliptical.

7. The carrier of claim 1, wherein the two outer surfaces of the substrate are plasma treated.

8. A cell culture system comprising at least one carrier of claim 1.

9. The cell culture system of claim 8, wherein the cell culture system is a bioreactor.

10. The cell culture system of claim 9, wherein the bioreactor comprises a fluid having a forced convective fluid motion.

11. The cell culture system of claim 9, wherein the bioreactor is a stirred tank bioreactor, or a reactor with a rocking or rolling motion.

12. A kit for culturing cells, comprising a disposable housing pre-loaded with the carrier of claim 1.

13. The kit of claim 12, wherein the disposable housing is a bag, a flask, a tube, a petri dish, or a bottle.

14. The carrier of claim 1, wherein at least one of the two outer surfaces of the substrate is modified with a gas plasma treatment comprising oxygen, nitrogen, nitrous oxide, ammonia, carbon dioxide, or combinations thereof prior to deposition of the hydrophilic, water soluble coating material.

15. The carrier of claim 1, wherein the carrier further comprises a macromolecular coating on the two outer surfaces of the substrate.

16. The carrier of claim 1, wherein the length is in a range from about 0.2 mm to about 6.5 mm, the width is in a range from about 0.2 mm to about 6.5 mm and the height is about 0.5 mm.

17. The carrier of claim 16, wherein the carrier has a length of about 6.5 mm, a width of about 6.5 mm and a height of about 0.5 mm.

18. The carrier of claim 1, wherein the length is in a range from about 0.2 mm to about 6.5 mm, the width is in a range from about 0.2 mm to about 6.5 mm and the height is in a range from about 1 mm to about 10 mm.

* * * * *